United States Patent [19]

Bunce et al.

[11] Patent Number: 4,935,564
[45] Date of Patent: Jun. 19, 1990

[54] PROCESS FOR PREPARING ALKYL HALIDES

[75] Inventors: Timothy R. Bunce, Madison, Ind.; Ronald S. Evanko, Carrollton, Ky.; Timothy G. Hueston, Midland, Mich.

[73] Assignee: Dow Corning Corporation, Midland, Mich.

[21] Appl. No.: 225,496

[22] Filed: Jul. 28, 1988

[51] Int. Cl.$^5$ ............................................. C07C 17/16
[52] U.S. Cl. ..................................... 570/258; 570/142
[58] Field of Search ................................. 570/258, 142

[56] References Cited

U.S. PATENT DOCUMENTS

| | | | |
|---|---|---|---|
| 1,918,371 | 7/1933 | Berndt et al. | 570/258 |
| 2,570,495 | 8/1946 | Scott | 570/258 |

Primary Exqminer—Howard T. Mars
Attorney, Agent, or Firm—Carl A. Yorimoto; James E. Bittell

[57] ABSTRACT

A process for preparation of an alkyl halide, RX, from reaction between the corresponding alcohol, ROH, and a hydrogen halide, HX, which improves conversion of the hydrogen halide to the alkyl halide in a single pass through a reactor. The process comprises (A) contacting and reacting the hydrogen halide with a stoichiometric excess of the alcohol in a plug-flow reactor in which flow of a mixture comprising unreacted alcohol, unreacted hydrogen halide, the alkyl halide, and water is co-current; and (B) isolating and separating the alkyl halide.

12 Claims, 1 Drawing Sheet

PROCESS FOR PREPARING ALKYL HALIDES

BACKGROUND OF THE INVENTION

This invention relates to an improved process for the preparation of alkyl halides from the corresponding alcohol and a hydrogen halide. More specifically, this invention relates to a process in which the conversion of the hydrogen halide is maximized in a single pass through a reactor.

The preparation of alkyl halides, particularly methyl chloride from the reaction of the corresponding alcohol with a hydrogen halide is known in the art. The by-products of the reaction are water and the corresponding dialkyl ether. Most known processes carry out the reaction with a stoichiometric excess of the hydrogen halide relative to the alcohol. As such, unreacted hydrogen halide must be discarded to the environment or recovered and recycled to the process. The recovery of the hydrogen halide, particularly hydrogen chloride (HCl) creates many processing difficulties. To begin with, HCl forms a minimum boiling azeotrope with water. Recovery and recycle of HCl is complicated by this azeotrope. Additionally, the very corrosive nature of aqueous HCl dictates that handling of this stream be held to a minimum. Finally, many known processes utilize catalysts to promote the reaction.

Steele et al., U.S. Pat. No. 3,981,938, issued Sept. 21, 1976, describes a process for producing alkyl halides by reacting the corresponding alcohol with at least a 10 mole percent excess of hydrogen halide. The reactants are passed through what Steele et al., call a "boiling bed" reactor. Under certain circumstances a "boiling bed" reactor can be considered to be a plug flow reactor. However, Steele et al., do not present sufficient information to make such a distinction. The vapors exiting the reactor are contacted with a liquid stream of alkyl halide saturated with hydrogen halide. The resulting vapor stream of alkyl halide and hydrogen halide is condensed. The alkyl halide and hydrogen halide are then separated by distillation.

Fukuda et al., Japanese Patent Publication O.P.I. 146,727/81, Published Sept. 10, 1982, describes a process in which dimethyl ether is reacted with excess hydrogen chloride in the presence of a metal compound catalyst, and wherein the unreacted hydrogen chloride and the resulting methyl chloride mixture are reacted with methanol to form additional methyl chloride. The reactor disclosed by Fukuda et al. is a column or columns packed with a solid catalyst. Fukuda et al. discloses that the reaction step in which unreacted hydrogen chloride is reacted with methanol is carried out with a stoichiometric excess of hydrogen chloride.

DESCRIPTION OF THE DRAWING

FIG. 1 outlines the process in which aqueous hydrogen chloride and a stoichiometric excess of methanol are contacted in a liquid phase in a plug-flow reactor in which backmixing of reactants, product methyl chloride, and by-product water is minimized. The desired methyl chloride product is separated and isolated; by-product water is separated from excess methanol, the water being discarded; and the excess methanol is recovered and recycled to the reactor.

In FIG. 1, 1 is the aqueous hydrogen chloride (HCl) feed to the reactor. 2 is a heat exchanger in which stream 1 is heated. 3 is the methanol feed to the reactor. 4 is a heat exchanger in which stream 3 is heated. 5 is a packed column in which the aqueous HCl, methanol, the product methyl chloride, and the by-product water flow upward through the reactor in a co-current, plug flow configuration. The heat input into heat exchangers 2 and 4 controls the temperature of the reactor 5. The temperature and pressure within the reactor 5 are controlled so that the reactants within the reactor are in a liquid, aqueous environment. Stream 6 is a vapor effluent from the reactor 5 which consists essentially of methyl chloride, methanol, and by-product dimethyl ether. Stream 7 is a liquid effluent from the reactor 5 which comprises mainly methanol, water, and a small amount of HCl. 8 is a distillation column in which methanol and methyl chloride are recovered as an overhead product stream 9. Stream 10 is a combination of the water fed with the aqueous HCl and by-product water and a small amount of HCl. Stream 10 is discarded. 11 is a condenser in which stream 9 is cooled. Streams 6 and 9 are fed to a distillation column 12 in which product methyl chloride is recovered as an overhead product stream 13. Excess methanol is recovered as a bottoms stream 14 from the distillation column 12. The recovered methanol stream 14 is recycled to the reactor.

SUMMARY OF THE INVENTION

Figure 1:
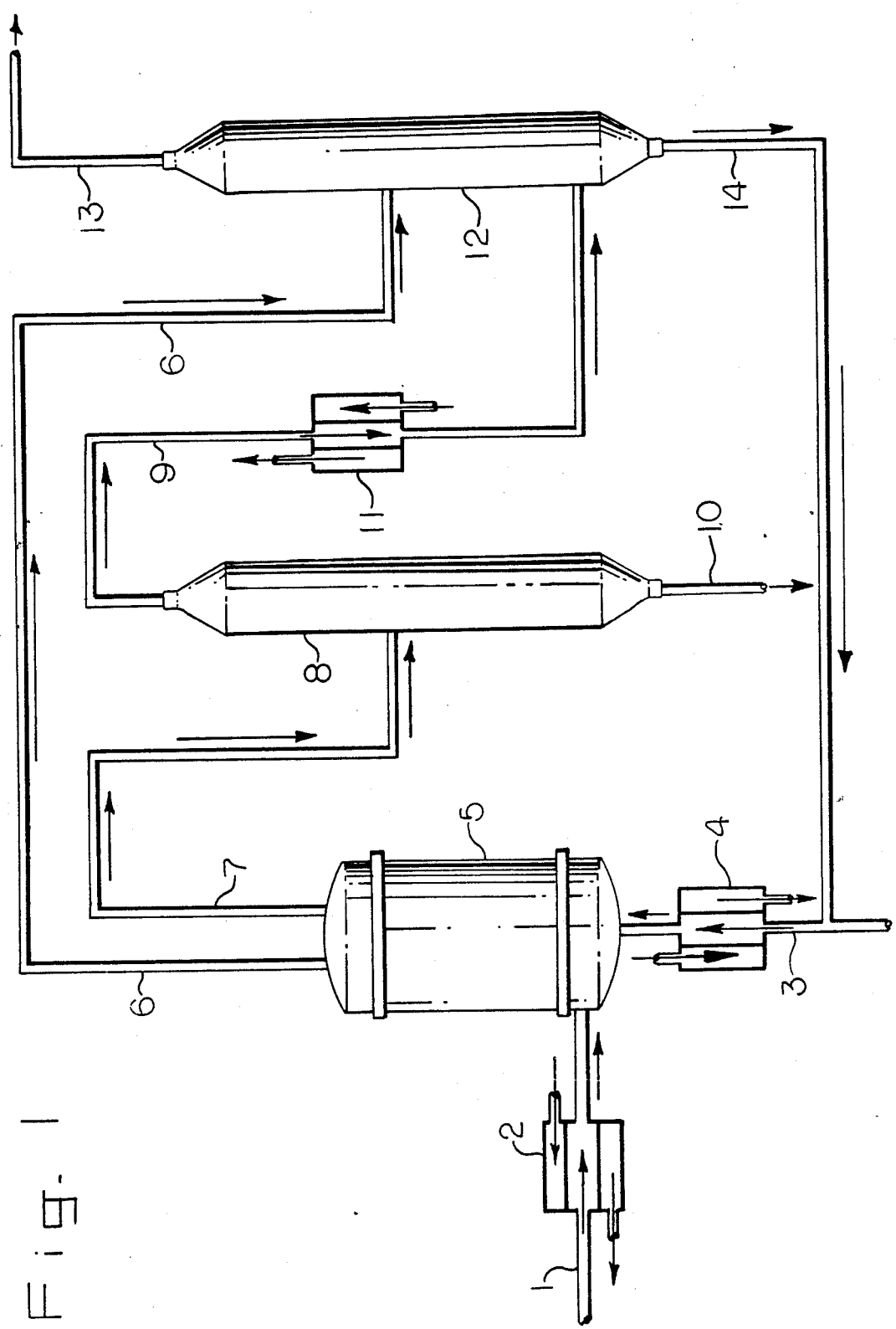
FIG. 1 is a representation of one embodiment of the instant invention. This representation is presented to be illustrative and is not to be construed as limiting the instant invention.

The objective of the instant invention is the preparation of an alkyl halide from the reaction of the corresponding alcohol and a hydrogen halide in which conversion of the hydrogen halide is maximized in a single pass through the reactor, eliminating the need for recovering and recycling hydrogen halide.

It has been found that high first-pass conversion of hydrogen halide at high rates of production can be achieved by using a reactor in which the reactants are fed co-currently into a plug-flow reactor configuration in which backmixing is minimized. Further the reaction takes place in an aqueous environment without a catalyst. The excess alcohol can be recovered and recycled to the reactor, and a very dilute stream of aqueous hydrogen halide is discarded.

DESCRIPTION OF THE INVENTION

In accordance with the instant invention there is provided a process for the preparation of an alkyl halide from the corresponding alcohol and a hydrogen halide under conditions that will be delineated herein. What is described, therefore, is a process for preparation of an alkyl halide, RX, from reaction between the corresponding alcohol, ROH, and a hydrogen halide, HX, in the absence of a catalyst, said process improving conversion of the hydrogen halide to the alkyl halide in a single pass through a reactor, wherein R is an alkyl group containing from 1 to 4 carbon atoms; and wherein X is a halogen atom;

said process comprising (A) contacting and reacting the hydrogen halide with a stoichiometric excess of the alcohol in a plug-flow reactor in which flow of a mixture comprising unreacted alcohol, unreacted hydrogen halide, the alkyl halide, and water is co-current; wherein the temperature within the reactor is greater than about 100° C., and pressure within the reactor is in a range from about 15 to 150 psig to maintain a liquid, aqueous medium in the reactor; and (B) isolating and separating the alkyl halide.

The reaction of an alcohol with a hydrogen halide can be represented as, $$ROH + HX = RX + H_2O \quad (1)$$

Additionally, dialkyl ether can form as a by-product by the reaction, $$ROH + ROH = R_2O + H_2O \quad (2)$$

The alcohol utilized in the instant invention can be, for example, methanol, ethanol, n-propanol, i-propanol, n-butanol, sec-butanol, or t-butanol. The alcohol can be brought to the reactor as a liquid by known means such as pumping. The alcohol may also be vaporized by conventional means and fed to the reactor as a vapor. The alcohol can be fed to the reactor as a vapor or liquid at multiple feed points or at just one point.

The hydrogen halide, utilized in the instant invention, can be, for example, hydrogen fluoride, hydrogen chloride, hydrogen bromide, or hydrogen iodide. Hydrogen chloride is the preferred hydrogen halide. The hydrogen halide can be fed as an aqueous solution or as an anhydrous gas. Aqueous hydrogen halide can be fed to the reactor by conventional means for transporting liquids such as pumping. The anhydrous HCl can be fed to the reactor by conventional means for transporting gases. For the purposes of the instant invention the term "essentially anhydrous hydrogen halide" refers a stream with only trace amounts of water, as for example, in the range 1000 ppm water or less.

The product alkyl halide can be, for example, methyl chloride, methyl bromide, ethyl fluoride, ethyl chloride, n-propyl chloride, n-propyl iodide, i-butyl chloride, or t-butyl chloride.

Unlike much of the prior art, the reaction of the alcohol and the hydrogen halide to produce the alkyl halide is effected in the absence of any catalyst, as for example, metal halide salts, activated alumina, etc.

The alcohol and the hydrogen halide are contacted in a plug-flow reactor (PFR) in which the flow of reactants and subsequent products and by-products is co-current. As known in the art, in a PFR there is essentially no mixing in the direction of flow, but with some mixing in the transverse direction. Therefore, there is a concentration gradient of reactants between the feed end and exit end of the reactor. In comparison, in a back-mixed reactor or continuous stirred tank reactor (CSTR), used extensively in the preparation of alkyl halides, the reactants, products, and by-products are totally mixed, and essentially no concentration gradient exists in the reactor. Reaction rate generally depends upon concentration of reactants. The PFR configuration takes advantage of the higher rates corresponding to the higher concentration of reactants at the feed end of the reactor. Therefore, the PFR will require a smaller reactor volume, shorter residence time, than that required for the more conventional CSTR.

The PFR can be, for example, known reactor configurations such as a packed bed, a tray-type column, or a series of small CSTR's with separation between reactors.

It has been found that feeding a stoichiometric excess of an alcohol relative to a hydrogen halide significantly improved the conversion of the hydrogen halide to the desired alkyl halide. It is preferred that the stoichiometric excess of the alcohol relative to the hydrogen halide be greater than about 10 mole percent to gain benefit from the instant invention. It is more preferred that the stoichiometric excess of the alcohol be in a range from about 20 to 200 mole percent. This preferred range gives a satisfactory balance between increased conversion of hydrogen halide to alkyl halide and the generation of by-product dialkyl ether. Hydrogen halide conversion to the desired alkyl halide has been found to increase from about 70 percent to as much as 95 percent. It is understood that lower stoichiometric excesses of alcohol approaching a stoichiometric balance can be utilized, however, with minimum increase in hydrogen halide conversion. It is further understood that stoichiometric excesses greater than 200 mole percent can be utilized, however, with potentially significant increases in the production of by-product dialkyl ether. However, it has been found that within the preferred range of stoichiometric excess of the alcohol and the reaction conditions disclosed by the instant invention the formation of dialkyl ether is acceptable and does not cause a significant raw material utilization or cost penalty.

Thus, the use of a stoichiometric excess of alcohol, as described above, facilitates improved conversion of hydrogen halide to the desired alkyl halide. Conversion of hydrogen halide is complete enough so that what hydrogen halide remains can be discarded without significant economic penalty. Thus, the desired conversion of the hydrogen halide is effected in a single-pass through the plug-flow reactor.

The reaction of the alcohol with the hydrogen halide should be carried out under conditions in which a liquid, aqueous medium exists within the reactor. It is preferred that the temperature within the reactor be in a range from about 100° to 200° C. It is further preferred that the pressure within the reactor system be in a range from about 15 to 150 pounds per square inch, gauge (psig).

The residence time of the liquid mixture in the reactor should be in a range from about 30 to 200 minutes. It is understood that residence times less than about 30 minutes can be used; however, reaction may not be complete. Residence times longer than 200 minutes can be utilized; however, the generation of by-product dialkyl ether would increase. Generally shorter residence times are preferred.

Isolating and separating the alkyl halide can involve, for example, (C) separating a vapor stream and a liquid stream from the mixture flowing through the reactor;

(D) separating alkyl halide from the vapor stream while recovering a first portion of unreacted alcohol; and (E) separating water from the liquid stream while recovering a second portion of unreacted alcohol;

(F) combining and recycling the first portion and the second portion of unreacted alcohol to the reactor; and (G) discarding a stream comprising water.

Separating vapor and liquid streams from the reactor can be effected by such known means as a separation chamber in which the reactor effluent is passed to allow vapor to separate from the liquid phase before or after reactor pressure is reduced. The alkyl halide can be separated and recovered from the vapor stream by cooling the vapor stream to condense unreacted alcohol and recovering both the alkyl halide and unreacted alcohol by distillation. Unreacted alcohol can be separated and recovered from the liquid phase by such known techniques as distillation. Recovered alcohol can be recycled to the reactor. The water resulting from the above separation along with a small amount of hydrogen halide, can be discarded.

The alkyl halide can be further handled by such known techniques as compressing and cooling to recover the alkyl halide as a liquified gas or liquid. The alkyl halide can be further processed by known means for removing dialkyl ethers.

So that those skilled in the art may better understand and appreciate the instant invention, the following examples are presented. These examples are presented to be illustrative and are not to be construed as limiting the claims presented herein.

EXAMPLE 1

A plug-flow reactor was constructed from 1.6-inch diameter zirconium pipe constructed in several sections, connected by flanged connections. Short spool sections at top and bottom enabled connections for inlet and outlet process streams and thermowells. The reactor was packed with 0.25 inch ceramic saddles to a depth of approximately 4 feet. The reactor was placed in a vertical position. Direction of the flow of materials was from the bottom of the reactor to the top. The reactor was wrapped with electrical heating tape.

Methanol and hydrochloric acid were fed as liquids from separate reservoirs. Methanol and hydrochloric acid feed were effected by separate positive displacement pumps. Both materials were fed separately to coils within a heated fluidized sand bath. Methanol was intended to be totally vaporized. Temperature within the reactor was controlled by the electrical input to both the sand bath and the heating tape. The heating tape balanced heat loss to assure adiobatic operation. Temperature and pressure of the reactor were monitored by conventional means. Product methyl chloride (MeCl), by-produced water and dimethyl ether (Me$_2$O), and unreacted methanol (MeOH), and hydrogen chloride (HCl) exited the top of the reactor as a mixture of vapor and liquid. The mixture of vapor and liquid exiting the reactor passed through an air-cooled coil. The cooled stream then went to a chamber, approximately 2 liters in volume, in which the vapor and liquid were separated. Reactor pressure was maintained with a pressure control valve downstream from the separation chamber. The liquid phase and the vapor phase were sampled at this point. The vapor stream passed through a water scrubber and then to the atmosphere.

In each run made, the system was operated until temperature and pressure reached an essentially steady state condition. Once an essentially steady state condition was reached the system was allowed to run for about 1.5 hours before sampling. Performance was monitored at steady state conditions by analyzing samples of the liquid and vapor streams after the water-cooled condenser. For the liquid stream, HCl was analyzed by conventional titration with base; MeOH content was determined by gas chromatographic (GC) analysis. For the vapor stream, analysis was effected by GC analysis. Typically, three samples of each stream were taken and the average of the results of analyses were taken. Analysis showed that essentially all the water which was fed with the aqueous HCl feed and all the water which formed as a by-product was in the liquid phase. Thus, an HCl/water balance of the liquid phase allowed calculation of the conversion of HCl to MeCl. A similar mass balance was performed to calculate Me$_2$O levels.

Three runs were made in which an aqueous solution of 17.7 weight percent HCl was used as the HCl feed. This solution was prepared by diluting commercially available concentrated hydrochloric acid with distilled water. The stoichiometric ratio of MeOH to HCl was varied from a ratio of about 1.0 to 1.5. These runs are designated as Samples A, B, and C. Temperature in the reactor for these runs was held at about 160° to 165° C. Reactor pressure was maintained at about 100 pounds per square inch, gauge (psig). Table 1 is a summary of the results of these three runs. In Table 1, the feed rates of aqueous HCl and MeOH, in kg/hr, are designated as "HCl" and "MeOH", respectively; the calculated residence time of the reactants within the reactor, in minutes, is designated "R.T."; the molar ratio of MeOH to HCl is designated as "Ratio"; the HCl content of the liquid phase, in weight percent, is designated "%HCl"; and the calculated conversion of HCl to MeCl, in percent conversion, is designated "Cl Conv".

TABLE 1

| Sample | HCl | MeOH | R.T. | Ratio | % HCl | Cl Conv |
|---|---|---|---|---|---|---|
| A | 0.95 | 0.16 | 72 | 1.09 | 4.0 | 72.2 |
| B | 0.85 | 0.16 | 79 | 1.22 | 3.1 | 82.2 |
| C | 0.66 | 0.16 | n.a. | 1.53 | 1.2 | 93.4 | n.a. = not available

The above results demonstrate that under the conditions of the above plug-flow reactor system, excess methanol significantly increases the conversion of hydrogen chloride to methyl chloride.

EXAMPLE 2

Using procedures and equipment similar to those utilized in Example 1, a series of runs was made to study the impact of MeOH to HCl ratio when utilizing concentrated hydrochloric acid. These runs are designated as Samples D, E, and F, respectively.

The concentrated hydrochloric acid used was commercially available 37 weight percent HCl. Reactor temperature was maintained at about 160° C. and reactor pressure was maintained at about 100 psig.

Table 2 is a summary of the results of these runs. The notation utilized in Example 1 as applied here. Additionally, in Table 2 the Me$_2$O content of the product MeCl is designated "%Me$_2$O".

TABLE 2

| Sample | HCl | MeOH | R.T. | Ratio | % HCl | Cl Conv | % Me$_2$O |
|---|---|---|---|---|---|---|---|
| D | 0.60 | 0.17 | 104 | 0.88 | 9.1 | 70.8 | 0.35 |
| E | 0.88 | 0.30 | 68 | 1.05 | 7.3 | 79.1 | 0.79 |
| F | 0.50 | 0.33 | 97 | 2.01 | 1.6 | 94.8 | 4.10 |

The above results further demonstrate that excess methanol improves the conversion of hydrogen chloride to methyl chloride using a plug-flow reactor configuration.

What is claimed is:

1. A process for preparation of an alkyl halide, RX, from reaction between the corresponding alcohol, ROH, and a hydrogen halide, HX, in the absence of a catalyst, in a single pass through a reactor,
    wherein R is an alkyl group containing from 1 to 4 carbon atoms; and wherein X is a halogen atom; said process comprising
    (A) contacting and reacting the hydrogen halide with a stoichiometric excess of the alcohol in a plug-flow reactor in which flow of a mixture comprising unreacted alcohol, unreacted hydrogen halide, the alkyl halide, and water is co-current; wherein the temperature within the reactor is greater than about 100° C., and the pressure within the reactor is in a range from about 15 to 150 psig to maintain a liquid, aqueous medium in the reactor; and (B) isolating and recovering the alkyl halide.

2. A process according to claim 1, wherein isolating and recovering the alkyl halide comprises (C) separating a vapor stream and a liquid stream from the mixture flowing through the reactor;

(D) separating alkyl halide from the vapor stream while recovering a first portion of unreacted alcohol; and (E) separating water from the liquid stream while recovering a second portion of unreacted alcohol;

(F) combining and recycling the first portion and the second portion of unreacted alcohol to the reactor; and (G) discarding a stream comprising water.

3. A process according to claim 1, wherein the hydrogen halide is fed to the reactor as an aqueous solution.

4. A process according to claim 1, wherein the hydrogen halide is fed to the reactor as an essentially anhydrous gas.

5. A process according to claim 1, wherein the stoichiometric excess of the alcohol is greater than about 10 mole percent relative to the hydrogen halide.

6. A process according to claim 5, wherein the stoichiometric excess of the alcohol is in a range from about 20 to 200 mole percent relative to the hydrogen halide.

7. A process according to claim 1 wherein contact temperature within the reactor is in a range from about 100° to 200° C.

8. A process according to claim 1, wherein contact time within the reactor is maintained at greater than about 30 minutes.

9. A process according to claim 8, wherein contact time within the reactor is maintained in a range from about 30 to 200 minutes.

10. A process according to claim 1, wherein the alkyl halide is methyl chloride, the alcohol is methanol, and the hydrogen halide is hydrogen chloride; the stoichiometric excess of the methanol is in a range from about 20 to 200 mole percent relative to the hydrogen chloride; the contact temperature within the reactor is in a range from about 100° to 200° C.; the pressure within the reactor is maintained in a range from about 15 to 150 pounds per square inch, gauge; the contact time within the reactor is maintained in a range from about 30 to 200 minutes.

11. A process according to claim 10, wherein the hydrogen chloride is fed to the reactor as an aqueous solution.

12. A process according to claim 10, wherein the hydrogen chloride is fed to the reactor as an essentially anhydrous gas.

* * * * *